(12) United States Patent
Dogariu et al.

(10) Patent No.: US 6,958,816 B1
(45) Date of Patent: Oct. 25, 2005

(54) MICRORHEOLOGY METHODS AND SYSTEMS USING LOW-COHERENCE DYNAMIC LIGHT SCATTERING

(75) Inventors: Aristide Dogariu, Winter Springs, FL (US); Gabriel Popescu, Brighton, MA (US); Raj Rajagopalan, Gainesville, FL (US)

(73) Assignee: Research Foundation of the University of Central Florida, Orlando, FL (US)

( * ) Notice: Subject to any disclaimer, the term of this patent is extended or adjusted under 35 U.S.C. 154(b) by 418 days.

(21) Appl. No.: 10/242,221

(22) Filed: Sep. 12, 2002

Related U.S. Application Data

(60) Provisional application No. 60/327,226, filed on Oct. 5, 2001.

(51) Int. Cl.[7] .................................. G01B 9/02
(52) U.S. Cl. ...................................... 356/479
(58) Field of Search .............................. 356/479, 497; 250/227.19, 227.27; 600/425

(56) References Cited

U.S. PATENT DOCUMENTS

| | | | |
|---|---|---|---|
| 5,155,549 A | 10/1992 | Dhadwal | 356/336 |
| 5,457,526 A | 10/1995 | Kosaka | 356/72 |
| 5,459,570 A | 10/1995 | Swanson et al. | 356/345 |
| 5,710,630 A * | 1/1998 | Essenpreis et al. | 356/479 |
| 5,751,424 A | 5/1998 | Bostater, Jr. | 356/342 |
| 5,986,277 A | 11/1999 | Boutque et al. | 250/554 |
| 5,991,697 A * | 11/1999 | Nelson et al. | 356/28.5 |
| 6,015,969 A | 1/2000 | Nathel et al. | 250/227.27 |
| 6,175,669 B1 | 1/2001 | Colston et al. | 385/12 |
| 6,201,608 B1 | 3/2001 | Mandella et al. | 356/491 |
| 6,525,823 B1 * | 2/2003 | Dogariu et al. | 356/479 |

OTHER PUBLICATIONS

Low-coherence interferometry of particles distributed in a dielectric medium, Brodsky et al, Journal of the Optical Society of America, Sep. 1997, pp. 2263-2268.*

Handbook of OCT, 2002, pp. 6-8.*

* cited by examiner

*Primary Examiner*—Samuel A. Turner
(74) *Attorney, Agent, or Firm*—Brian S. Steinberger; Law Offices of Brian S. Steinberger, P.A.

(57) ABSTRACT

Methods and systems for using dynamic light scattering, for investigating local rheological responses of complex fluids over a frequency range larger than that provided by standard instrumentation. A low-coherence radiation source is used with fiber optics to allow measurements of small volume spacing of up to approximately $1/10$ of a picoliter. The methods and systems are based on dynamic light scattering, for investigating the local rheological response of a complex fluid over a frequency range larger than that provided by standard mechanical instrumentation. The low-coherence radiation used in a fiber optics configuration allows the measurements to be confined to a small volume around a tenth of a picoliter. The ability of the method to accurately measure both loss and storage moduli has been tested using both simple Newtonian liquids and viscoelastic, complex fluids. Monitoring liquid-gel transitions in polymer solutions has also been demonstrated. The unique capability of the technique to localize the measurement volume can be used for three-dimensional mapping of rheological properties in heterogeneous systems. Other embodiments can use open-air setups instead of optical fibers to transmit and receive the low coherence light.

41 Claims, 11 Drawing Sheets

MICRORHEOLOGY METHODS AND SYSTEMS USING LOW-COHERENCE DYNAMIC LIGHT SCATTERING

This invention relates to dynamic light scattering, and in particular to methods and systems for using low-coherence light sources with an optical fiber probe to investigate rheological effects such as loss and storage moduli parameters liquids, and this invention claims the benefit of U.S. Provisional application 60/327,226 filed Oct. 5, 2001.

BACKGROUND AND PRIOR ART

Through present date, a broad range of rheological instrumentation exists for applications in food products, paints and coatings, polymers and composites, asphalt, pharmaceuticals, electronic materials, etc. For specific purposes, special viscometers such as an oscillating capillary viscometer, automated rolling ball viscometer and a high shear capillary viscometer are now being used. However, there are problems with using rheological instrumentation for soft type materials.

Soft materials, which include polymer solutions, surfactant solutions, and biological materials, among others, are characterized by complex structures with multiple characteristic time and length scales; thus their response to external strains has a nontrivial time dependence. One of the most important descriptors of these properties is the complex shear modulus G(t), which is typically measured in the frequency domain. The real part G'(ω) in the frequency domain describes the elastic storage property of the system, while the imaginary part G"(ω) is a measure of the viscous loss behavior. The ability to measure locally the mechanical response of a material to an applied shear strain has a variety of potential applications, especially in biology, where the mechanical properties of the cells and intracellular matter are of utmost importance.

Recently a number of techniques have been developed or suggested for probing the rheological properties of complex materials at a microscopic scale, an area that has come to be known as microrheology. F. C. MacKintosh and C. F. Schmidt, Curr. Opin. In Coll. Interface Sci. 4, 300. Most of the microrheological techniques rely on applying a strain to the fluid through embedded "probe" particles, and the strains result either from imposed force on the probe. Application of an external force, such as a magnetic field, to the particles may produce a nonlinear response of the fluid since the resulting strain could be substantial, whereas strains resulting from thermally excited probes are quite low and ensure linearity of response in most of the cases. The probe motion is quantified by its mean-squared displacement, which can be obtained by particle tracking, single-particlemicroscopy, or dynamic light scattering (e.g., diffusing wave spectroscopy, when multiple scattering is dominant. See F. Amblard, A. C. Maggs, B. Yurke, A. N. Pargellis, and S. Leibler, Phys. Rev. Lett. 77, 4470(1996); T. G. Mason, K. Ganesan, J. H. Van Zanten, D. Wirtz, and S. C. Kuo, Phys. Rev. Lett. 79, 3282(1997); F. Gittes, B. Schnurr, P. D. Olmsted, F. C. MacKintosh, and C. F. Schmidt, Phys. Rev. Lett. 79, 3286 (1997); and T. G. Mason and D. A. Weitz, Phys. Rev. Lett. 74, 1250(1995). It is important to note that recording individual particle trajectories typically requires a smaller sample volume than in the case of diffusing wave spectroscopy [DWS], in which the measurements are performed over an ensemble of particles.

Dynamic light scattering (DLS) techniques have the advantage of providing an inherent average over the particle ensemble, while single-particle techniques require successive measurements in order to obtain a reliable average. It is worth noting that atomic force microscopy (AFM) can also be used in this context. H. Ma, J. Jimenez, and R. Rajagopalan, Langmuir, 16, 2254(2000). Here, one monitors the thermal fluctuations of the tip of the AFM cantilever instead of following a probe particle. While an AFM allows one to examine microrheology at interfaces as do particle-tracking techniques or the dynamic light scattering technique this invention is that the analysis of the AFM data is not straightforward for a number of reasons. Most notable among these are the complicated geometry of the probe and the AFM tip and the influence of the intrusive, mechanical behavior of the AFM cantilever itself and the resulting, often ill-characterized, fluid response. H. Ma, J. Jimenez, and R. Rajagopalan, Langmuir, 16, 2254(2000).

Microrheological measurements have been reported in the last few years for a number of materials, e.g., colloidal dispersions, polymer solutions, and biological cells and materials.

For example, numerous experiments on action networks have shown nontrivial high-frequency dependence of the shear modulus and models have been proposed to explain such behavior. See F. Gittes and F. C. MacKintosh, Phys. Rev. E. 58, R1241(1998); D. C. Morse, Phys. Rev. E. 58, R1237(1998); and J. Xu, A. Palmer, and D. Wirtz, Macromolecules 31, 6486(1998).

It is commonly agreed that most viscoelastic fluids have shear moduli that follow a power-law dependence in the high-frequency region, but the actual value of the exponent appears to vary depending on the materials and, sometimes, the experimental technique used. More recently, it has been shown that cross correlating the thermal motion of pairs of embedded particles offers a more precise and a different way of examining the microrheology of soft condensed matter, suggesting that measurements using previous microrheological techniques may need to be revised or reexamined. See for example, J. C. Crocker, and M. T. Valentine, E. R. Weeks, T. Gisler, P. D. Kaplan, A. G. Yodh, and D. A. Weitz, Phys. Rev. Lett. 85, 888(2000); A. J. Levine and T. C. Lubensky, Phys. Rev. Lett. 85, 1774(2000); and G. Popescu and A. Dogariu, Opt. Lett. 26, 551(2001). Therefore, it is of great interest to find complementary investigation methods for high-frequency viscoelastic behavior of complex fluids at microscopic scales.

For measuring rheological properties, various patents have also been proposed over the years. See for example, U.S. patents: U.S. Pat. No. 5,155,549 to Dhadwal; U.S. Pat. No. 5,457,526 to Kosaka; U.S. Pat. No. 5,459,570 to Swanson et al.; U.S. Pat. No. 5,751,424 to Bostater, Jr.; U.S. Pat. No. 5,986,277 to Bourque et al.; U.S. Pat. No. 5,991,697 to Nelson et al.; U.S. Pat. No. 6,015,969 to Nathel et al.; U.S. Pat. No. 6,175,669 to Colston et al. and U.S. Pat. No. 6,201,608 to Mandella et al. However, the entire prior art systems have various deficiencies.

All the conventional methods generally rely on sensing the effect of a macroscopically-induced mechanical stress. The frequency ranges of these prior art systems are generally limited at several kHz. The prior art systems generally require relatively large volumes of material (at least a few micro-liters) to be available for analysis. For rheological analysis of biological media, the available prior art instrumentation requires sample manipulation and preparation.

To the inventors' knowledge, there are no applicable real in-situ methods systems available to overcome the problems described above.

SUMMARY OF THE INVENTION

The first object of the invention is to provide microrheology methods and systems of using low-coherence dynamic light scattering that does not require external actions and instead relies on the mechanical stress induced by Brownian motion of the "seed" particles or scattering centers existing in complex fluids.

The second object of the invention is to provide microrheology methods and systems having no frequency limitations of use where at least several hundred kHz can be easily obtained.

The third object of the invention is to provide microrheology methods and systems that use extremely small measurement volumes such as up to no more than approximately 0.1 picoliters.

The fourth object of the invention is to provide microrheology methods and systems that use fiber optics for in-situ analysis that offers high degrees of experimental flexibility and applicability. For example, the novel invention can also be used for on-line sensing in industrial environment applications.

The fifth object of the invention is to provide microrheology methods and systems that allows for properties under investigation to be able to be probed locally to reveal detailed information about its morphology.

The sixth object of the invention is to provide microrheology methods and systems that allow the investigation of rheological properties of biological materials in vitro and as well as in vivo.

The invention includes various embodiments of microrheology systems. Some of the embodiments include using low-coherence dynamic light scattering that include a low coherence light source, a single mode optical fiber having one end adjacent to the light source, and a second disposed within a small volume of liquid, the fiber for transmitting an emission from the light source into the small volume of liquid and a detector attached to the optical fiber for analyzing mechanical properties of the small volume of liquid which can be up to approximately a few picoliters, such as approximately $1/10^{th}$ of a picoliter.

The low coherence light source can be a superluminescent diode. The detector can be a spectrum analyzer for analyzing a frequency domain of the fluctuations within the volume of the liquid. Alternatively, the detector can be an autocorrelator for analyzing the temporal domain of the fluctuations within the volume of the liquid, wherein the frequency domain can include a KHz frequency range. Additionally, a computer can be used as the detector.

The liquid being analyzed by the systems can include biological fluid, such as synovial fluid, biopolymer fluid, protein fluid and/or blood. Still furthermore, the invention can be used with other fluids such as but not limited to ink fluids, polymer fluids, thickener fluids, hydrocolloid fluids, and oil.

The mechanical properties being analyzed by the systems can include but not be limited to elasticity, viscosity, viscoelasticity, and the like.

The detector can also map three-dimensional distributions of the mechanical properties. Additionally, the detector can include a time correlator for analyzing a temporal autocorrelation of the volume of the liquid.

Another embodiment of the microrheology system can include a fiber splitter, and a reference fiber attached to the fiber splitter, and additionally a reference mirror attached to an end of the reference fiber.

A still another embodiment of the microrheology system using low-coherence dynamic light scattering can include a low coherence light source, an open air transmission medium having a beam splitter and a reference mirror wherein the light source is transmitted into the small volume of liquid, and a detector attached adjacent the open air transmission medium for analyzing mechanical properties of the small volume of liquid. The embodiment can also include a focusing lens for focusing the light source into the small volume of the liquid such as a volume range of up to approximately a few picoliters such as approximately $1/10^{th}$ of a picoliter.

Further objects and advantages of this invention will be apparent from the following detailed description of a presently preferred embodiment, which is illustrated, schematically in the accompanying drawings.

The results obtained using approximately 0.1 microns on the same samples are represented by the dashed lines.

Figure 2A:
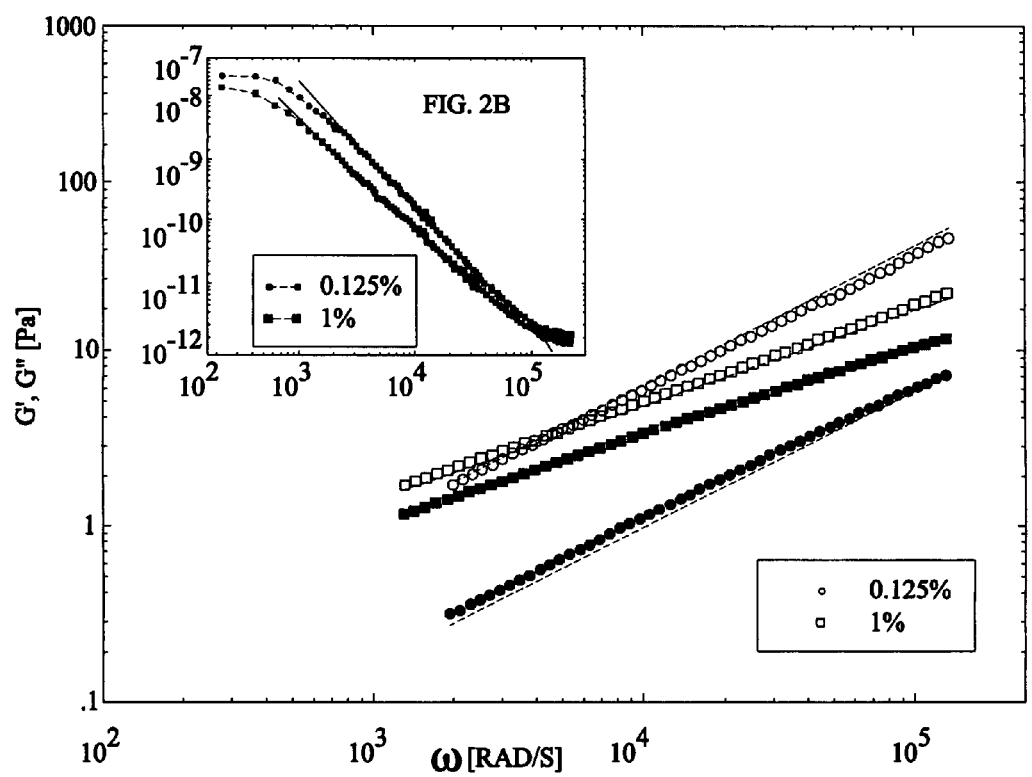
FIG. 2A shows a graph of the modulit G'(closed symbols) and G"(open symbols) versus angular frequency for PEO (polyethylene oxide) solutions of two different concentrations by mass obtained using approximately 0.2 micron particles.

FIG. 2B shows a graph of the raw power spectra corresponding to the same polymer solutions as that shown in FIG. 2A.

Figure 3A:
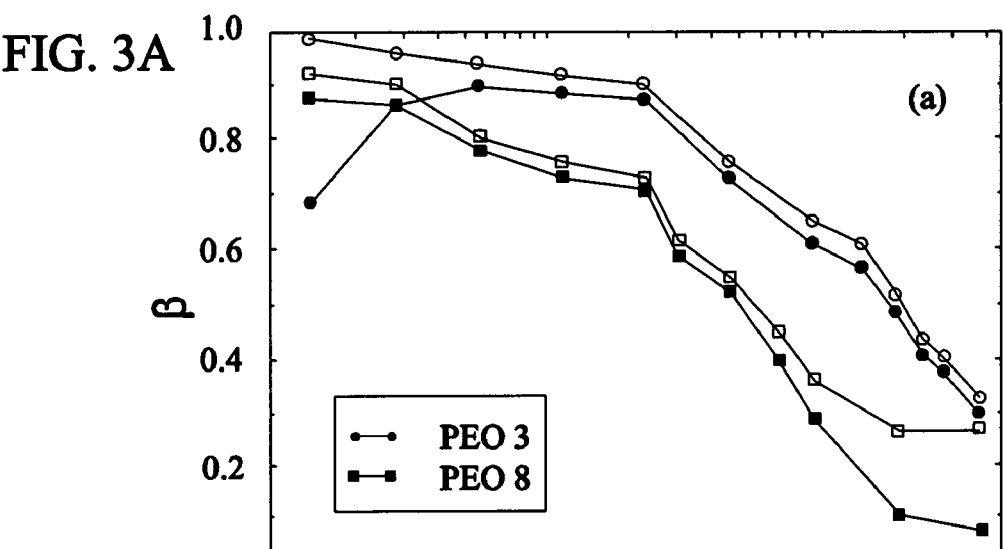

FIG. 3A shows a graph of the exponent B and loss tangent g as functions of the PEO concentration for two molecular weights where the power-law dependence of G'(closed symbols) and G"(open symbols) on frequency, as indicated, where the parameter B was obtained by fitting G'(w) and G"(w) with the function awb.

Figure 3B:
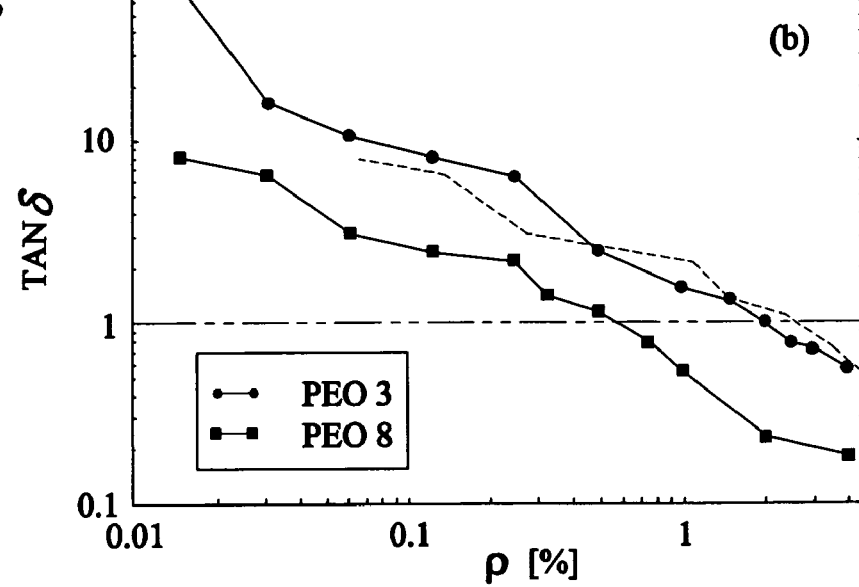

FIG. 3B shows a graph of the loss tangent for the same solutions as in FIG. 3A measured as the ratio G"(w)/G'(w) corresponding to an angular frequency of 10 to $4^{th}$ rad/s, where the dashed line represents the data associated with the molecule PEO 8 after multiplying the concentration variable by 4.25.

Figure 4:
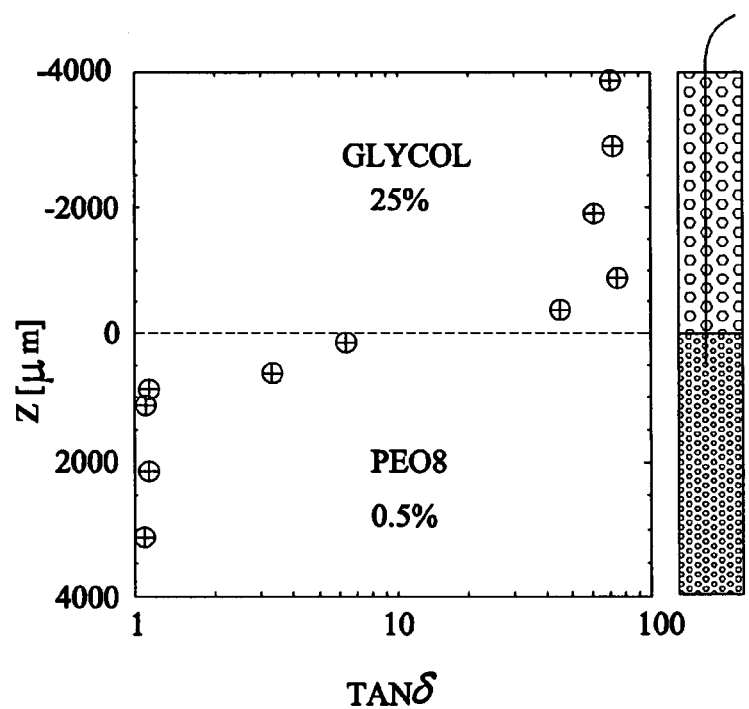

FIG. 4 shows a graph of the loss tangent (measured in FIGS. 3A–3B) as a function z-coordinate, as the fiber penetrates from a layer of simple liquid (approximately 25% by volume of ethylene glycol) to a complex fluid (approximately 0.5% by mass of PEO8).

Figure 5:
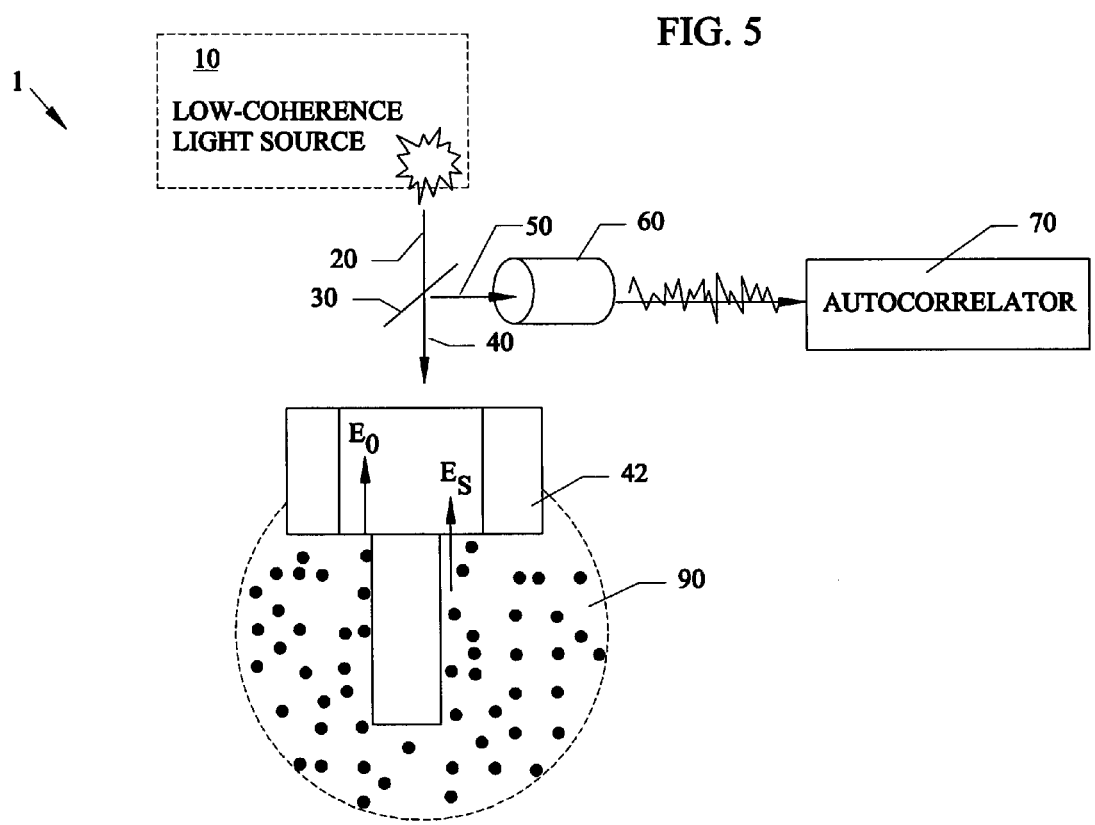

FIG. 5 shows a general layout of the low-coherence light source and fiber optic probe and measuring volume using the invention.

Figure 6:
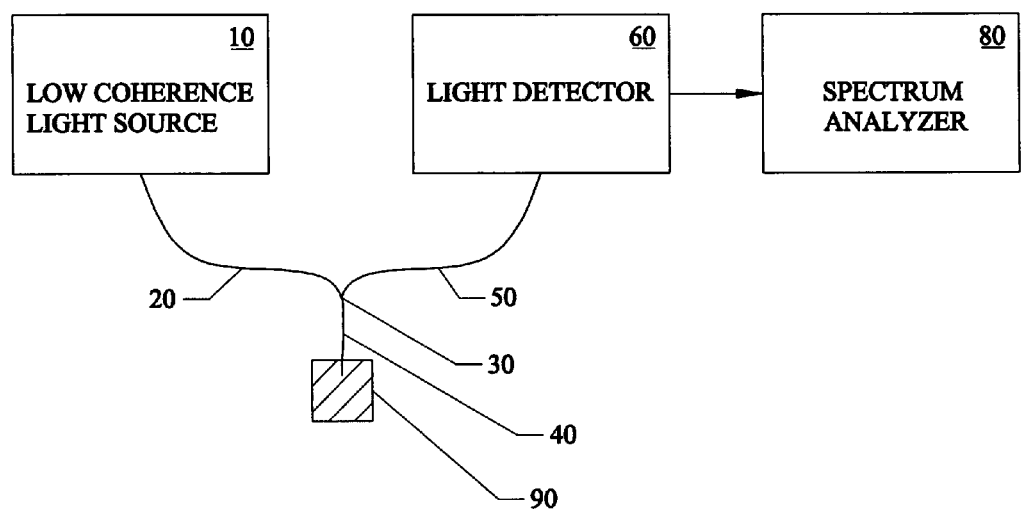

FIG. 6 shows a first preferred embodiment of the microheology low-coherence light scattering invention used with a medium to be tested using a spectrum analyzer.

Figure 7:
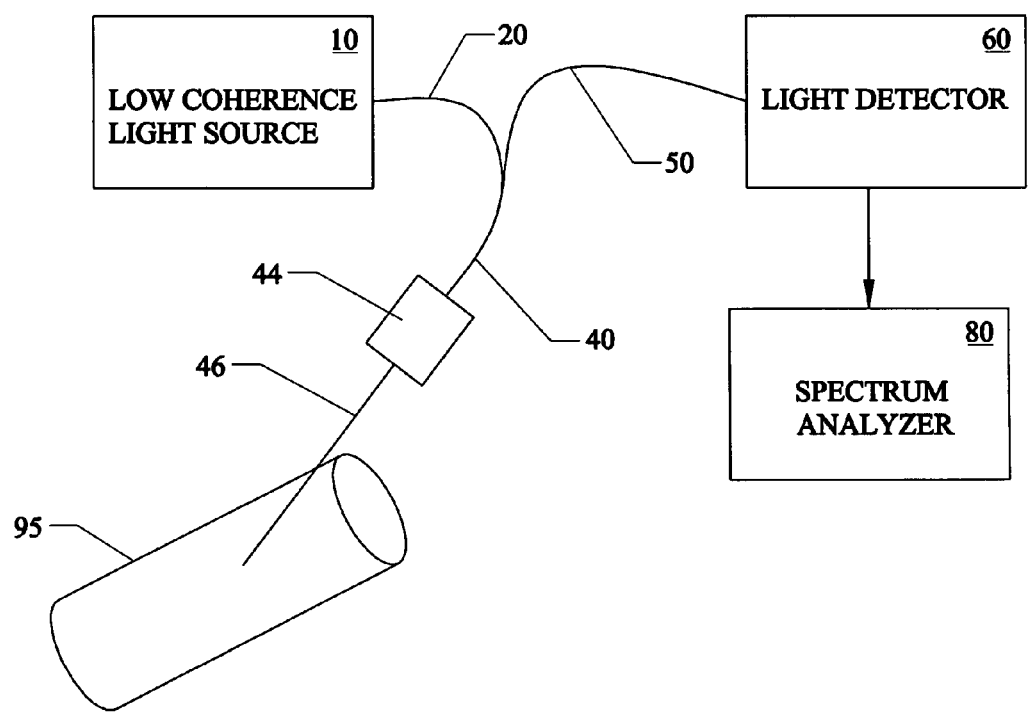

FIG. 7 shows the first preferred embodiment of FIG. 6 being applied to a vein.

Figure 8:
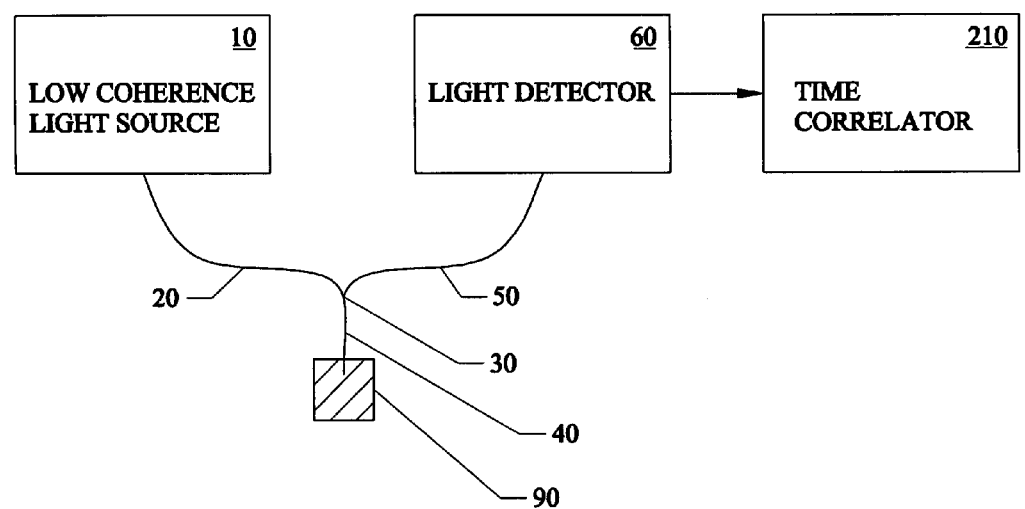

FIG. 8 shows a second preferred embodiment of the microrheology low-coherence light scattering invention used with a medium to be tested using a time correlator.

Figure 9:
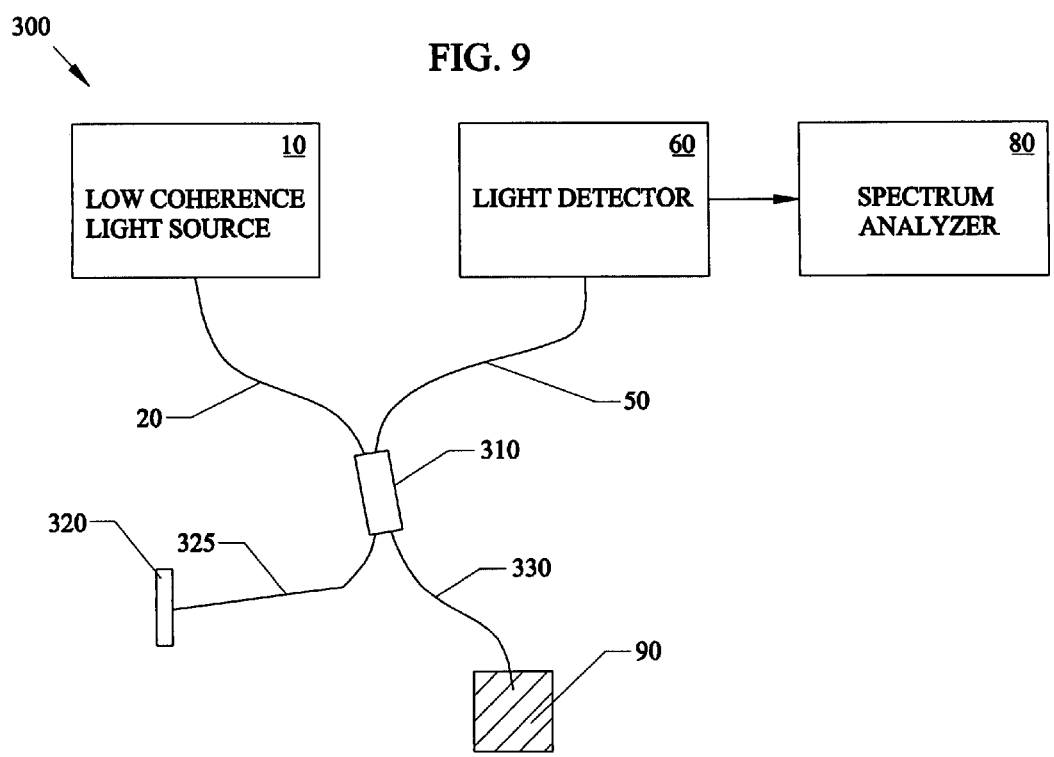

FIG. 9 shows a third preferred embodiment of the microheology low-coherence light scattering invention using a fiber splitter and reference mirror.

Figure 10:
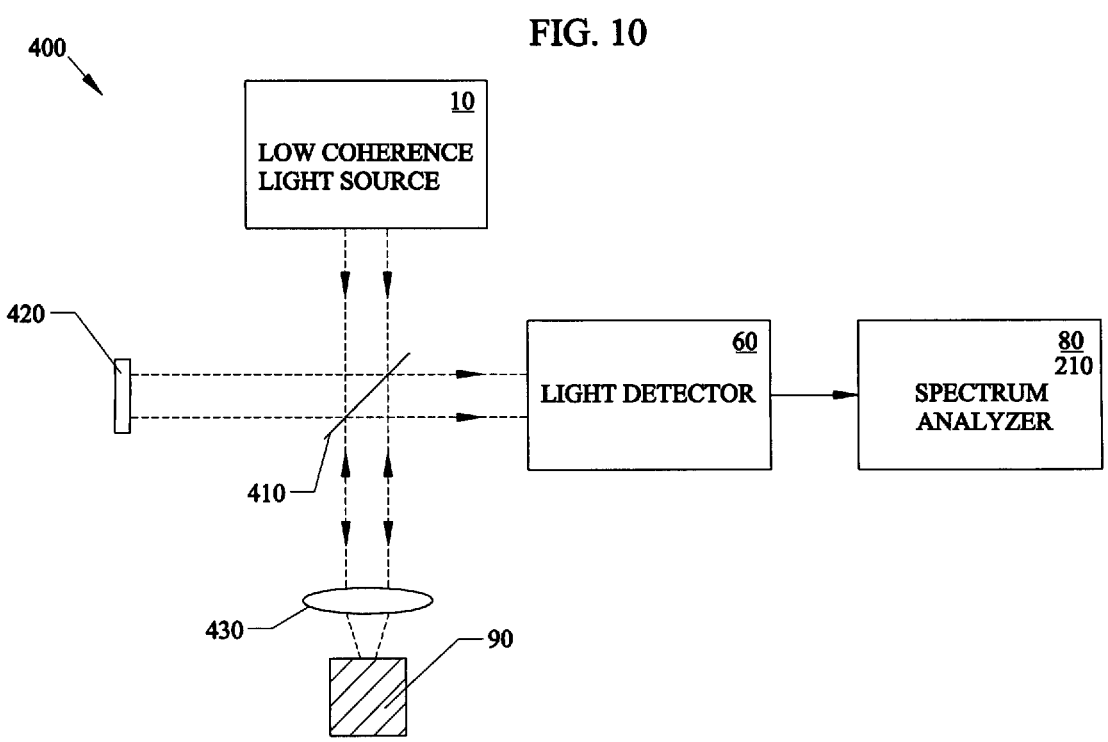

FIG. 10 shows a fourth preferred embodiment of the microheology low-coherence light scattering invention using an open-air setup with focusing lens.

Figure 11:
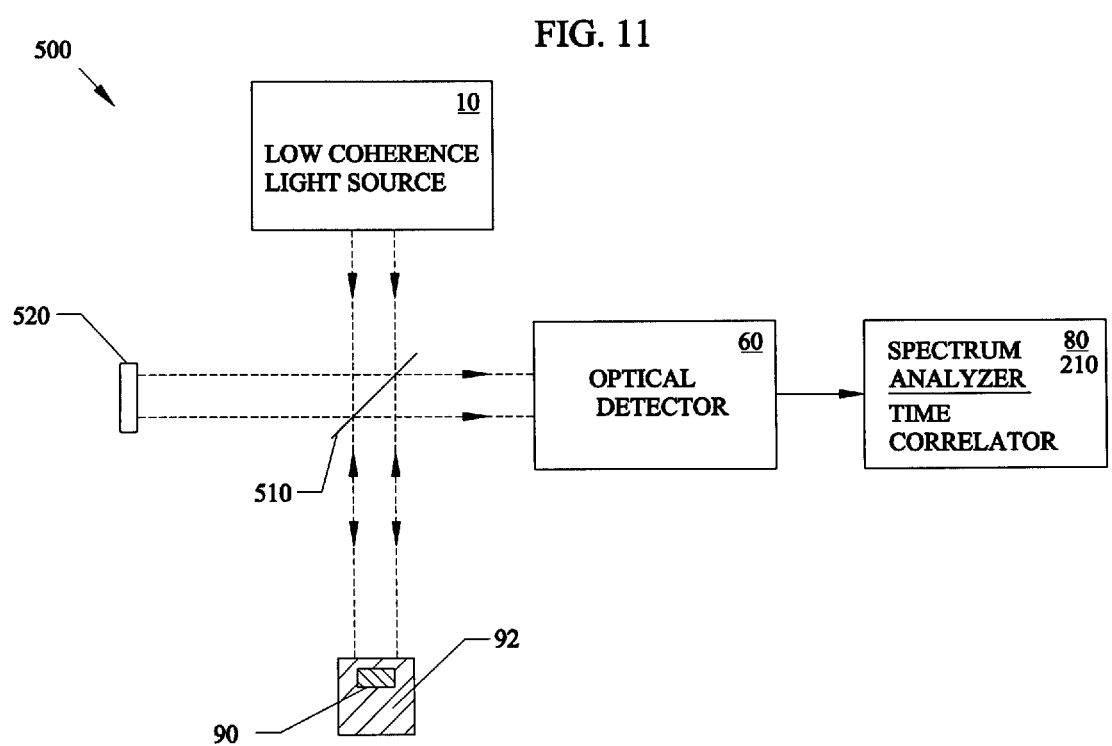

FIG. 11 shows a fifth preferred embodiment of the microheology low-coherence light scattering invention using an open-air setup without any focusing lens.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The invention relies on quantifying the motion of thermal particles embedded in the fluid under investigation. The system measures the dynamical properties of the fluid, including analyzing fluctuations within the fluid in the frequency domain and the temporal domain. By combining the properties of partially coherent light that is guided in a single-mode optical fiber, the high-frequency power density $\Delta r2(\omega)$ of the embedded particles can be extracted. The measurement volume is of the order of approximately a tenth of a picoliter. The microrheological information can be obtained using the fluctuation-dissipation theorem that relates $\Delta r2(\omega)$ with the loss response as defined in equation 1.

$$\chi''(\omega) = \frac{\omega}{2k_B T} \langle \Delta r^2(\omega) \rangle. \tag{1}$$

where kB is Boltzmann's constant, and T is the absolute temperature of the material. Due to causality, the storage X' (w) and loss response X' (w) are related through the KramersKronig relationship as shown in equation (2):

$$\chi'(\omega) = \frac{2}{\pi} P \int_0^\infty \chi''(\xi) \frac{\xi}{\xi^2 - \omega^2} d\xi. \tag{2}$$

where P indicates the principal value integral.

The inventors have tested this new technique on a variety of systems with rheological properties ranging from purely viscous solutions to materials with highly viscoelastic behavior. By taking advantage of the spatial coherence properties of a single-mode fiber and the limited temporal coherence of a broadband source, the measurement volume is isolated at the end of an optical fiber, and it was shown that, due to the reduced dimensions of the measurement volume, the novel invention technique provides accurate results for the particle diffusion coefficient and concentration and is not affected by multiple scattering even for optically dense suspensions.

A main characteristic of this dynamic light scattering scheme is that the properties of the system under investigation are probed locally, which can reveal detailed information about its morphology. In addition, the optical fiber(s) access can offer a high degree of experimental flexibility, enlarging the range of applicability. It is also important to emphasize another significant advantage offered by the elimination of multiple scattering effects in the proposed technique.

The novel invention shows the local loss and elastic response of a complex fluid can be inferred as a result of thermal excitation produced by the probe particles.

FIG. 5 shows a general layout 1 of the low-coherence light source 10 and fiber optic probe 40 in the measuring volume 90 using the invention. The light source 10 emits along optical fiber 20 to beam splitter 30 so that a probe portion of the optical fiber 40 has a lower probe end 42 which is directly inserted into the volume 90 to be measured such as a complex viscoelastic fluid (such as but not limited to polyethylene oxide (PEO) solutions of various concentrations and molecular weights, which can be on the order of up to approximately 0.1 pico liter. A light detector 60 such as Nirvana, NewFocus Inc., can then be sent to an autocorrelator such as a Brookhaven BI 2000.

First Preferred Embodiment

FIG. 6 further describes a first preferred embodiment 100 of a low-coherence radiation being emitted by a low-coherence light source 10 such as a superluminescent diode which can be coupled into a single-mode optical fiber 20, which represents one arm a 1×2 fiber coupler 20, 30, 40, 50. The output 42 of the coupler can be immersed in the fluid 90 under investigation. The light backscattered by the probe particles can be collected through the same fiber 40 through fiber 50 to the detector 60 and the signal can be analyzed in the frequency domain by a spectrum analyzer 80 such as SR760.

The signal detected is an interference of two electromagnetic fields: the fluctuating field backscattered by the particles undergoing thermal motion and the static field due to Fresnel reflection at the fiber-fluid interface. The fluctuating light can be detected only from the coherence volume, defined by the coherence length and the transversal dimension of the fiber core, in which the optical fields preserve relative phase correlations. In the inventors experiments, the central wavelength of the broadband light as $\lambda$=824 nm, while the coherence length had a value $l_c$=30 $\mu$m. For this geometry, the relationship between the normalized intensity $g^{(2)}$ and amplitude $g^{(1)}$ autocorrelation functions has he form in equation 3 as follows:

$$g^{(2)}(\tau) = 1 + \gamma g^{(1)}(\tau). \tag{3}$$

The numerical coefficient $\gamma$ relates to the average intensities associated with the Fresnel component and the scattered light from the coherence volume, respectively.

Throughout our experiments, the photon mean free path in the medium was always much longer than the coherence length of the light used. Thus, within the coherence volume, the single scattering regime applies and the first-order autocorrelation function can be written as equation (4).

$$g^{(1)}(\tau) = \exp\left[-\frac{1}{6} q^2 \langle \Delta r^2(\tau) \rangle\right]. \tag{4}$$

where q is the scattering vector associated with our backscattering geometry, and $\Delta r^2$ is the mean square displacement of the particles under thermal motion.

In the inventors experiments, the measurable quantity is the power spectrum of the scattered light fluctuations $P(\omega)$, which is the Fourier counterpart of $g^{(2)}$. At this point, we make the observation that, in the high-frequency region, P(ω) is directly related to the power spectral density of the particle displacements as shown in equation (5).

$$P(\omega) = \frac{\gamma q^2}{6} \langle \Delta r^2(\omega) \rangle. \quad (5)$$

Equation (5) holds for times of evolution much shorter that the characteristic decaying time of the autocorrelation function, when equation (4) can be linearized as equation 6.

$$G(\omega) = \frac{1}{6\pi a} \frac{1}{\chi(\omega)}. \quad (6)$$

This approximation is similar to the first cumulant expansion used in deriving the Laplace relationship between the autocorrelation function and the path length probability distribution. Therefore, it is rather surprising that the microrheological experiments based on the DWS (diffusing wave spectroscopy) technique provided accurate results even for long times of evolution.

In the frequency domain, the applicability of equation 5 lies in the high-frequency domain, beyond the characteristic width of the power spectrum P(ω). The criteria of applicability for this approximation, as they apply for specific experimental situations, will be discussed in more detail below. With this approximation, it becomes apparent that the high-frequency dependence of the shear modulus Gω) can be obtained by combining equations (1), (2), (5) into equation 6.

$$G(\omega) = \frac{1}{6\pi a} \frac{1}{\chi(\omega)}. \quad (6)$$

where a is the radius of the probe particles. Thus, by inferring the mechanical frequencies from the measured electrical frequencies via equation (5), the rheological information can be obtained in the frequency domain directly.

It is important to note that the time scale in the following graphs describes the dynamic fluctuations of the medium through which the light travels, and not the length of time the light travels a medium as used in prior art systems. The system measures the dynamical properties of the fluid, which are fluctuations within the fluid which are then analyzed in the frequency domain and/or the temporal domain.

Figure 1:
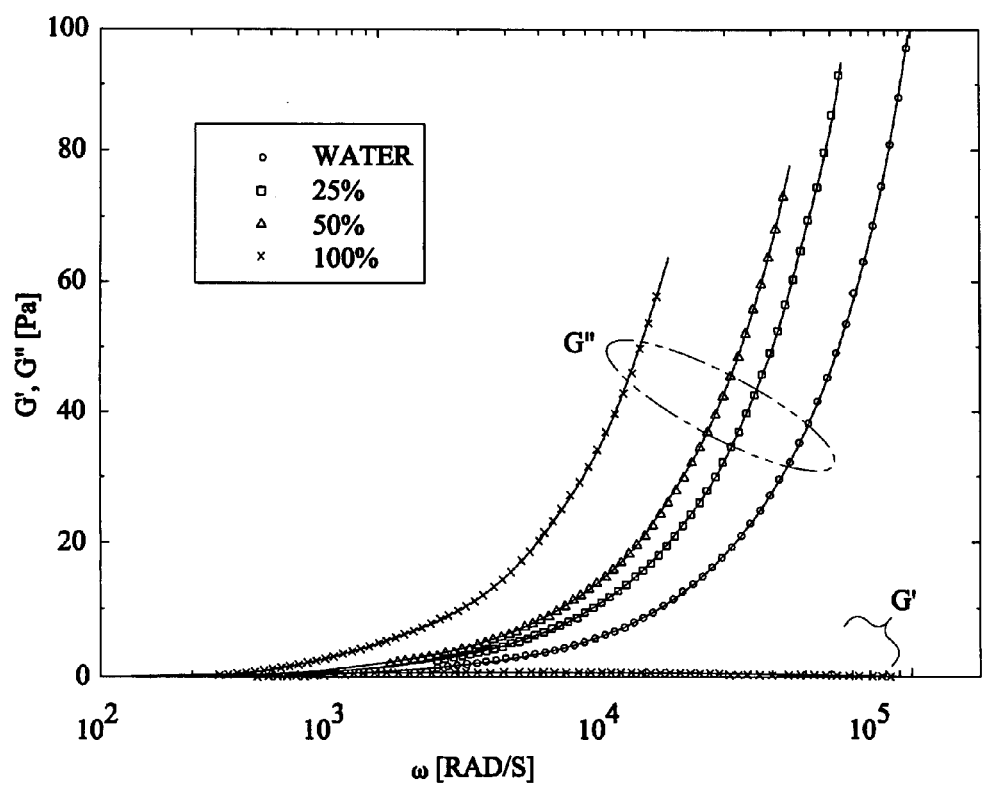
FIG. 1 shows a graph of the loss and storage shear moduli for water and aqueous suspensions of ethylene glycol at different volume fractions. The continuous lines indicate the fit with $\omega^1$ dependence.

FIG. 1 shows a graph of the loss and storage shear moduli for water and aqueous suspensions of ethylene glycol at different volume fractions. It is important to note that the standard power-law behavior of the rheological properties of viscous fluids is fully recovered FIG. 2A shows a graph of the modulit G'(closed symbols) and G"(open symbols) versus angular frequency for PEO (polyethylene oxide) solutions of two different concentrations by mass obtained using approximately 0.2 micron particles.

When this behavior is compared with results shown for purely viscous fluids shown in FIG. 1, one notices that even a small fraction of PEO molecule dissolved in water changes the microrheological properties of the solution. The dashed lines in FIG. 2 represents the results for the same fluids, now seeded with particles of diameter 0.1 microns and the results are almost indistinguishable from the data obtained with 0.2 microns particles, suggesting an excellent agreement between the measurements with particles of different dimensions.

FIG. 2A shows a graph of the raw power spectra corresponding to PEO polymer solutions of different concentrations FIG. 3A shows a graph of the exponent B and loss tangent g as functions of the PEO concentration for two molecular weights where the power-law dependence of G'(closed symbols) and G"(open symbols) on frequency, as indicated, where the parameter B was obtained by fitting G'(w) and G"(w) with the function awb.

FIG. 3B shows a graph of the loss tangent for the same solutions as in FIG. 3A measured as the ratio G"(w)/G'(w) corresponding to an angular frequency of 10 to $4^{th}$ rad/s, where the dashed line represents the data associated with the molecule PEO8 after multiplying the concentration variable by 4.25.

The experiments were performed on aqueous solutions of PEO over a broad range of concentrations and with two different molecular weights: $3.10^6$ (PEO 3), and $8.10^6$ (PEO 8), with concentrations by weight from 0.0125% $ to 4%. The results for the shear modulus and loss tangent are summarized in FIGS. 3a \& b. It can be seen that for the lower molecular weight PEO (PEO 3), viscous behavior is found in the region of low polymer concentrations. This region is characterized by an almost linear frequency dependence of G"(ω), while G'(ω), is small in magnitude (large δ) and displays weaker dependence on frequency. Judging from the data in FIG. 3, we conclude that, for PEO 3 molecules, considerable entanglement appears around a concentration of 0.05%. At the other end of the concentration interval, for the heavier molecule (PEO 8), G(ω), has an almost flat dependence on frequency, while the associated loss tangent decreases to values significantly smaller than unity. This transition to a gel-like behavior is less developed for the PEO 3 solutions, which require higher concentrations for the liquid-to-gel transition.

FIG. 4 shows a graph of the loss tangent (measured in FIGS. 3A–3B) as a function z-coordinate, as the fiber penetrates from a layer of simple liquid (approximately 25% by volume of ethylene glycol) to a complex fluid (approximately 0.5% by mass of PEO8).

A particular advantage of the experimental arrangement and technique proposed is the possibility of probing viscoelastic changes through an interface as a function of spatial position within the interface. FIG. 4 demonstrates the ability to measure local rheological properties of various complex fluids; it shows that detailed information about the liquid-gel transition can be obtained with the approach proposed.

FIG. 5 shows a general layout of the low-coherence light source and fiber optic probe and measuring volume using the invention. The system is configured to measure dynamic properties of the fluid under test. What is measured, is the fluctuations produced by the fluid. Owing to the refractive-index contrast between the fiber core and the suspension solvent, the signal that is detected has two components: the light that is backscattered from the dynamic system and the component that is due to the Fresnel reflection at the fiber-medium interface. The coherence length and the transversal dimension of the fiber core define a coherence volume in which the optical fields preserve relative phase correlations.

FIG. 6 shows a first preferred embodiment of the microheology low-coherence light scattering invention used with a medium to be tested using a spectrum analyzer. Without additional optical components, the signal is detected and further analyzed in the frequency domain by a spectrum analyzer. A low coherence light source is coupled into a single-mode optical fiber, which represents one arm of a 1×2 fiber coupler. The output of the coupler is immersed in the colloidal suspension under investigation, and the backscattered light is collected through the same fiber.

FIG. 7 shows the first preferred embodiment 100 of FIG. 6 being applied 100A to a vein 95 using a coupler 44 for a needle probe 46.

Second Preferred Embodiment

FIG. 8 shows a second preferred embodiment 200 of the microheology low-coherence light scattering invention used with a medium to be tested using a time correlator 210. The other components in FIG. 8 are identical to and function similar to that of the previous figures.

Referring to FIG. 8, the analysis of the dynamic signal originating in the picoliter volume 90 can be performed in the time domain. Instead of a frequency analyzer one could use a temporal correlator 210 (for instance Brookhaeven 2-000) to obtain the temporal autocorrelation function of the fluctuating signal. It is known that between time and frequency domains there is a strict relationship determined by a conventional Fourier transformation. The entire analysis described before can be performed in the time domain using data provided by a time correlator.

Third Preferred Embodiment

FIG. 9 shows a third preferred embodiment 300 of the microheology low-coherence light scattering invention using a fiber splitter 310 and reference mirror 320.

Referring to FIG. 9, the reference field can be provided by another fiber 325 as shown in the figure. In this case, the reflection from the end of the fiber in contact with the medium is suppressed by, for instance, angle cut. A two-by-two fiber optic splitter 310 can be used to provide the necessary reference filed. Reflection from the end of the fourth fiber 325 or from an external mirror 320 at this end can provide the reference field. This embodiment eliminates the reflectivity requirement in the measurement fiber. The rest of the operation is functionally identical with the previous embodiments.

Fourth Preferred Embodiment

FIG. 10 shows a fourth preferred embodiment 400 of the microheology low-coherence light scattering invention using an open-air setup with focusing lens 430 such as a ×10 microscope objective. The invention can also be used without optical fibers. In this case, an open-air optical setup can have light from the low-coherence optical source 10 be focused onto the medium 90 to be tested. A reference mirror 420 such as a Newport flat in conjunction with a beam splitter 410 can produce the reference field as shown in the figure.

The focal plan of the lens 430 doesn't necessarily need to coincide with the coherence volume but when these are overlapped the signal could be maximized. Reflection from the sample is reflected off the beamsplitter 410 and combined with the reference field reflected off the mirror 420. An optical detector 60 collects the fluctuating interference signal and further processing is realized with a signal analyzer 80 or, alternatively, with a time correlator 210 (previously described).

Fifth Embodiment

FIG. 11 shows a fifth preferred embodiment 500 of the microheology low-coherence light scattering invention using an open-air setup without any focusing lens that is used in FIG. 10. Similar to the previous embodiment, the michrorheometer can be used without using optical fibers. In this case, an open-air optical setup can have light from the low-coherence optical source be collimated and impinge onto the medium 90 to be tested. A reference mirror 520 can be used in conjuncture with a beam splitter 510 to produce the reference field as shown in the figure. In this case the coherence volume 90 can be determined by width of the illuminating beam and the coherence length of the radiation. The position of the reference mirror 520 can determine the position of this coherence volume 90 inside the tested medium 92. A typical width of the illuminating beam could be one millimeter and a typical value of the coherence length could be 30 microns. The coherence volume generated can be placed, by adjusting the reference mirror, at approximately several millimiters behind within the scattering medium.

Referring to FIG. 11, reflection from the sample 90 can be reflected off the beamsplitter 510 and combined with the reference field reflected off the mirror 520. An optical detector 60 collects the fluctuating interference signal and further processing is realized with a signal analyzer 80 or, alternatively, with a time correlator 210 (as previously described). This embodiment 500 can have the advantage that is completely noninvasive. i.e. no optical element is in contact with the medium to be tested and the position of the measurement volume is adjusted by simply adjusting the position of the reference mirror 520.

While the preferred embodiments describe using superluminescent diodes (SLD), the invention can be used with other low-coherence light sources. For example, the invention can use Multiple quantum well LED (light emitting diodes)/SLD (superluminescent diodes). Furthermore, the invention can use Laser-pumped fluorescent organic dyes. Still furthermore, the invention can use Modelocked Ti:Al2O3 lasers. Still furthermore, the invention can be used with Superfluorescent optical fibers (ER, TM, ND/Yb doped).

The invention has applicability to the morphology of biological fluids having viscoelastic properties such as blood, synovial fluids, biopolymers, protein solutions, and the like.

The invention can have applicability to industrial rheology. A broad range of fluids such as but not limited to inks, polymers, thickeners and hydrocolloids with significant industrial relevance that are characterized by their rheological properties The invention can be used with distributed industrial sensing of such properties.

Furthermore, the invention can be used for flow induced morphology of complex fluids such as but not limited to liquid crystalline polymers (defects, complex geometries), immiscible polymers, blends (drop deformation, phase inversion, concentrated blends), suspensions (dispersion of porous agglomerates, flow of gel suspensions), polyolefines (orientation, morphology), and the like.

The invention can be used with fluids which are scattering due to their intrinsic morphology (complex fluids containing particulates, air bubbles, foams, emulsions, biofluids containing cells, and the like). The invention can also be used with fluids that do not scatter light but instead are "seeded" with scattering centers by adding additional small particles (micron sized, and the like) that act as probes for the mechanical properties of the fluid, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A microrheology system using low-coherence dynamic light scattering comprising:
   a low coherence light source;
   a single mode optical fiber having one end adjacent to the light source, and a second disposed within a small volume of liquid, the fiber for transmitting an emission from the light source into the small volume of liquid; and
   a detector attached to the optical fiber for analyzing mechanical properties of the small volume of liquid to retrieve rheological properties of the small volume of liquid by measuring mechanical properties, selected from a group consisting of: elasticity, viscosity and viscoelasticity, with a detector.

2. The microrheology system of claim 1, wherein the small volume of liquid includes:
   a volume range of up to approximately a few picoliters.

3. The microrheology system of claim 2, wherein the picoliter volume size includes:
   up to approximately $1/10^{th}$ of a picoliter.

4. The microrheology system of claim 1, wherein the low coherence light source is selected from at least one of:
   a superluminescent diode (SLD), a multiple quantum well light emitting diode (MQWLED), a modelocked Ti:Al2O3 laser, a laser pumped fluorescent organic dye, and a superfluorescent optical fiber.

5. The microrheology system of claim 1, wherein the detector further includes:
   a spectral analysis for analyzing a frequency domain of fluctuations within the volume of the liquid.

6. The microrheology system of claim 1, wherein the detector further includes:
   a time autocorrelation analysis for analyzing the temporal domain of the fluctuations within the volume of the liquid.

7. The microrheology system of claim 5, wherein the frequency domain includes:
   a KHz frequency range.

8. The microrheology system of claim 1, wherein the liquid includes:
   biological fluid.

9. The microrheology system of claim 7, wherein the biological fluid includes:
   synovial fluid.

10. The microrheology system of claim 7, wherein the biological fluid includes:
    biopolymer fluid.

11. The microrheology system of claim 7, wherein the biological fluid includes:
    protein fluid.

12. The microrheology system of claim 1, wherein the fluid includes:
    blood.

13. The microrheology system of claim 1, wherein the fluid includes:
    ink fluids.

14. The microrheology system of claim 1, wherein the fluid includes:
    polymer fluids.

15. The microrheology system of claim 1, wherein the fluid includes:
    thickener fluids.

16. The microrheology system of claim 1, wherein the fluid includes:
    hydrocolloid fluids.

17. The microrheology system of claim 1, wherein the fluid includes:
    oil.

18. The microrheology system of claim 1, wherein the fluid includes:
    fluids which are scattering due to intrinsic morphology of the fluids.

19. The microrheology system of claim 18, wherein the fluids are selected from at least one of: complex fluids containing particulates, air bubbles, foams, emulsions, and biofluids containing cells.

20. The microrheology system of claim 1, wherein the fluid includes:
    fluids seeded with scattering centers that scatter light.

21. The microrheology system of claim 20, wherein the fluids include:
    small particles acting as probes for the mechanical properties of the fluid.

22. The microrheology system of claim 1, wherein the mechanical properties includes: elasticity.

23. The microrheology system of claim 1, wherein the mechanical properties includes: viscosity.

24. The microrheology system of claim 1, wherein the mechanical properties includes: viscoelasticity.

25. The microrheology system of claim 1, wherein the volume of liquid includes:
    a larger volume of liquid in which the small volume of liquid moves within.

26. The microrheology system of claim 1, wherein the detector includes:
    means for mapping three dimensional distributions of the mechanical properties.

27. The microrheology system of claim 1, wherein the single mode optical fiber further comprises:
    a fiber splitter; and
    a reference fiber attached to the fiber splitter.

28. The microrheology system of claim 27, further comprising:
    a reference mirror attached to an end of the reference fiber.

29. A microrheology system using low-coherence dynamic light scattering comprising:
    a low coherence light source;
    an open air transmission medium having a beam splitter and a reference mirror wherein the light source is transmitted into the small volume of liquid; and
    a detector attached adjacent the open air transmission medium for measuring and analyzing dynamic properties of the small volume of liquid by measuring and analyzing fluctuations in the small volume of liquid in at least one of the frequency domain and the temporal domain.

30. The microrheology system of claim 29, further comprising:
    a focusing lens for focusing the light source into the small volume of the liquid.

31. The microrheology system of claim 29, wherein the small volume of liquid includes:
   a volume range of up to approximately a few picoliters.

32. The microrheology system of claim 31, wherein the picoliter volume size includes:
   up to approximately $1/10^{th}$ of a picoliter.

33. The microrheology system of claim 29, wherein the fluid includes:
   fluids which are scattering due to intrinsic morphology of the fluids.

34. The microrheology system of claim 33, wherein the fluids are selected from at least one of: complex fluids containing particulates, air bubbles, foams, emulsions, and biofluids containing cells.

35. The microrheology system of claim 29, wherein the fluid includes:
   fluids seeded with scattering centers that do not scatter light.

36. The microrheology system of claim 35, wherein the fluids include:
   small particles acting as probes for the mechanical properties of the fluid.

37. A method of using low-coherence dynamic light scattering for microrheology applications, comprising the steps of:
   generating low coherence light from a light source;
   transmitting the generated light into a small volume of liquid; and
   measuring mechanical properties from fluctuations within the small volume of liquid with a detector when the generated light travels through the small volume of liquid.

38. The method of claim 37, wherein the transmitting step includes the step of:
   providing a single mode optical fiber having one end adjacent the generated light, and a second disposed within the small volume of liquid for receiving the generated light.

39. The method of claim 37, wherein the transmitting step includes the step of:
   providing an open air transmission medium having a beam splitter and a reference mirror wherein the generated light is transmitted into the small volume of liquid.

40. The method of claim 37, wherein the small volume of liquid includes:
   a volume range of up to approximately a few picoliters.

41. The method of claim 37, wherein the step of analyzing includes the step of:
   analyzing the liquid for at least one of: elasticity, viscosity and viscoelasticity.

* * * * *